(12) United States Patent
Su et al.

(10) Patent No.: US 8,575,292 B2
(45) Date of Patent: *Nov. 5, 2013

(54) HYDROXYL-FUNCTIONAL CARBAMOYL ORGANOSILICON COMPOUNDS OF LOW VOC AND HAP GENERATING POTENTIAL, ANTI-CORROSION AND/OR ADHESION PROMOTING COATING COMPOSITION CONTAINING SAME, ENVIRONMENTALLY BENIGN METHOD OF COATING METAL THEREWITH AND RESULTING COATED METAL

(75) Inventors: Shiu-Chin H. Su, Croton-on-Hudson, NY (US); Suresh K. Rajaraman, Newburg, NY (US); Alexander S. Borovik, White Plains, NY (US); Kendall L. Guyer, Carmel, NY (US); Eric R. Pohl, Mount Kisco, NY (US)

(73) Assignee: Momentive Performance Materials Inc., Waterford, NY (US)

( * ) Notice: Subject to any disclaimer, the term of this patent is extended or adjusted under 35 U.S.C. 154(b) by 1166 days.

This patent is subject to a terminal disclaimer.

(21) Appl. No.: 11/789,258

(22) Filed: Apr. 24, 2007

(65) Prior Publication Data

US 2008/0268146 A1    Oct. 30, 2008

(51) Int. Cl.
  *C08G 77/18*   (2006.01)
  *C08G 77/26*   (2006.01)
  *C07F 7/10*   (2006.01)

(52) U.S. Cl.
  USPC ............ 528/38; 556/406; 556/413; 556/414; 556/417; 556/419; 556/420; 556/436; 556/443; 556/465; 556/482; 528/33; 428/447; 428/450

(58) Field of Classification Search
  USPC ........................................................ 427/207
  See application file for complete search history.

(56) References Cited

U.S. PATENT DOCUMENTS

| | | | |
|---|---|---|---|
| 4,645,846 A | 2/1987 | DePasquale et al. | |
| 5,196,487 A | 3/1993 | Kogure et al. | |
| 5,206,285 A | 4/1993 | Castellucci | |
| 5,371,262 A | 12/1994 | Arkles | |
| 5,587,502 A * | 12/1996 | Moren et al. | 556/420 |
| 5,693,371 A | 12/1997 | Rodzewich et al. | |
| 5,709,957 A | 1/1998 | Chiang et al. | |
| 5,711,996 A | 1/1998 | Claffey | |
| 5,728,203 A | 3/1998 | Vorse et al. | |
| 5,750,197 A | 5/1998 | van Ooij et al. | |
| 5,759,629 A | 6/1998 | van Ooij et al. | |
| 5,801,217 A | 9/1998 | Rodzewich et al. | |
| 5,866,651 A | 2/1999 | Moren et al. | |
| 5,997,954 A | 12/1999 | Decker et al. | |
| 6,001,945 A | 12/1999 | Decker et al. | |
| 6,071,566 A | 6/2000 | Brown et al. | |
| 6,106,901 A | 8/2000 | Song et al. | |
| 6,121,404 A | 9/2000 | Liles | |
| 6,132,808 A | 10/2000 | Brown et al. | |
| 6,361,592 B1 | 3/2002 | Song et al. | |
| 6,369,139 B1 | 4/2002 | Osterholtz et al. | |
| 6,461,682 B1 | 10/2002 | Crotty et al. | |
| 6,534,568 B1 * | 3/2003 | Katz et al. | 523/212 |
| 6,699,586 B2 * | 3/2004 | Edelmann et al. | 428/447 |
| 7,875,318 B2 * | 1/2011 | Borovik et al. | 427/387 |
| 2005/0245753 A1 | 11/2005 | Cruse et al. | |
| 2006/0036034 A1 * | 2/2006 | Chaves et al. | 525/100 |
| 2006/0041063 A1 | 2/2006 | Cruse et al. | |
| 2006/0177657 A1 | 8/2006 | Weller | |
| 2006/0178451 A1 * | 8/2006 | Weller | 523/212 |
| 2006/0178487 A1 | 8/2006 | Weller | |
| 2006/0205907 A1 | 9/2006 | Guyer | |
| 2006/0293480 A1 | 12/2006 | Landon et al. | |

FOREIGN PATENT DOCUMENTS

WO    WO01/98403 A2    5/2001
WO    WO 2008/008077 A    1/2008

OTHER PUBLICATIONS

Elkin, et al., "Synthesis and Characterization of Novel Hydroxyalkyl Carbamate and Dihydroxyalkyl Carbamate Terminated Poly(dimethylsiloxane) Oligomers and their Block Copolymers with Poly(.epsilon.-caprolactone)", Macromolecules, 2006, vol. 39(25), pp. 8659-8668.

Smetankina, et al., "Reactivity of Organosilicon Diisocyanates. XXVII. Carbofunctional Organosilicon Compounds", Zhurnal Obshchei Khimii, 1974, vol. 44(12), pp. 2684-2688.

Novikova, et al., "Effect of the Association of OH-Groups of a Hydroxyl-Containing Component on the Kinetics of the Urethane Formation Reaction", Dopovidi Natsional 'Noi Akademii Nauk Ukraini, 1998, vol. 12, pp. 148-151.

Kuzetsova, et al., "Poly(ether urethanes) modified with a vinyl copolymer and organosilicon compounds", Zhurnal Prikladnoi Khimii, 1998, vol. 71(3), pp. 476-479.

Novikova, et al., "Association of OH Groups in the Multicomponent System of Hydroxyl-Containing Molecules and its Effect on the Formation of Polyurethanes", Vysokomolekulyarnye Soedineniya, Seriya A I Seriya B, 1998, vol. 40(5), pp. 878-883.

U.S. Appl. No. 11/358,550, filed Feb. 21, 2006, Chaves et al.
U.S. Appl. No. 11/358,818, filed Feb. 21, 2006, Chaves et al.
U.S. Appl. No. 11/358,369, filed Feb. 21, 2006, Chaves et al.
U.S. Appl. No. 11/358,861, filed Feb. 21, 2006, Chaves et al.

(Continued)

Primary Examiner — Marc Zimmer

(74) Attorney, Agent, or Firm — Dominick G. Vicari; Joseph S. Ostroff

(57) ABSTRACT

There is provided a hydroxyl-functional carbamoyl organosilicon compound, an anti-corrosion and/or adhesion promoting coating composition based thereon, a method for coating a metal surface employing the coating composition and the resulting coated metal article.

34 Claims, No Drawings

(56) References Cited

OTHER PUBLICATIONS

U.S. Appl. No. 11/505,221, filed Aug. 10, 2006, Chaves et al.
U.S. Appl. No. 11/598,906, filed Nov. 14, 2006, Pohl.
U.S. Appl. No. 11/505,166, filed Aug. 10, 2006, Chaves et al.
U.S. Appl. No. 11/505,055, filed Aug. 10, 2006, Chaves et al.
U.S. Appl. No. 11/505,178, filed Aug. 10, 2006, Chaves et al.
U.S. Appl. No. 11/544,132, filed Oct. 6, 2006, Chaves et al.
U.S. Appl. No. 11/544,142, filed Oct. 6, 2006, Chaves et al.

* cited by examiner

US 8,575,292 B2

HYDROXYL-FUNCTIONAL CARBAMOYL ORGANOSILICON COMPOUNDS OF LOW VOC AND HAP GENERATING POTENTIAL, ANTI-CORROSION AND/OR ADHESION PROMOTING COATING COMPOSITION CONTAINING SAME, ENVIRONMENTALLY BENIGN METHOD OF COATING METAL THEREWITH AND RESULTING COATED METAL

BACKGROUND OF THE INVENTION

1. Field of the Invention

This invention relates to organosilicon compounds, to anti-corrosion and/or adhesion promoting coating compositions made therefrom and methods for their application to metals and to metals possessing anti-corrosion and/or adhesion promoting coatings based on organosilicon compounds.

2. Description of the Prior Art

Most metals are susceptible to some form of corrosion, in particular atmospheric corrosion, resulting in the formation of various types of rust. Such corrosion may significantly affect the quality of a metal. Although superficial corrosion can usually be removed from metal surfaces, processes for its removal tend to be time consuming, costly and may have a negative impact on the integrity of the metal. Where coatings are applied to metal surfaces, corrosion of the metal may result in inadequate or ineffective adhesion between the coating and the metal surface. A reduction in adhesion between a coating and metal surface to which the coating has been applied may likewise lead to corrosion of the metal.

Metals of many kinds, including metal alloys, metal laminates, metal composites, and, the like, are widely used in manufacturing and construction. Certain types of metal, particularly ferrous metals such as iron and steel, often develop rust during storage and shipment. Rust (also called "storage stain") is typically caused by moisture which condenses on the surface of the metal there to react with the metal or metal coating on the metal. Rust is aesthetically unappealing and often impairs the ability of the metal to directly undergo subsequent processing operations. Thus, prior to conducting any subsequent processing operations, rust often needs to be removed from the surface of metal and the metal surface treated to prevent rust from reforming. Various methods are currently employed to not only prevent the formation of rust during shipment and storage, but also to prevent the formation of rust after the metal has undergone subsequent processing operations.

It is well known that prevention of rust on metals during their storage, shipping and use can be achieved by applying to their surfaces a thin film such as one of chromate. While chromate coatings do provide resistance to the formation of rust, chromium is highly toxic and environmentally undesirable. Furthermore, a chromium layer will not necessarily improve the adhesion of any subsequent layer applied thereto.

The rusting of metal can also be prevented or inhibited during storage, shipment and use by applying an aqueous solution of a hydrolyzable silane to the surface of the metal and thereafter curing the silane to provide a durable, adherent protective coating. Such a coating, however, may generate one or more volatile organic compounds (VOCs) and/or Hazardous Air Pollutants (HAPs) during hydrolysis of the silane. VOCs and HAPs are environmentally undesirable and governmental agencies have implemented regulations intended to limit the amounts of VOCs and HAPs materials. These regulations often require the purchase, installation and maintenance of expensive air purification equipment. Exposure to VOCs and HAPs can also be detrimental to the health and safety of workers due to their potential toxicity and flammability.

Therefore, there exists a need for a coating composition and a coating method for the protective treatment of metals that does not utilize chromium and that generates essentially no, or at most, very little VOCs or HAPs while still imparting desirable anti-corrosion and adhesion properties to the treated metals.

BRIEF DESCRIPTION OF THE INVENTION

It has now been discovered that greatly improved anti-corrosion and/or adhesion promoting properties for metals can be provided by coating compositions based on the hereinafter described hydroxyl-functional carbamoyl organosilicon compounds.

In accordance with the present invention, there is provided a hydroxyl-functional carbamoyl organosilicon compound which possesses:

(i) at least one hydroxyl group bonded to a carbon atom and at least one carbamoyl group covalently bonded to a silicon atom through a silicon-carbon bond, and (ii) at least one divalent oxygen-containing group possessing at least two silyloxy bonds.

Further in accordance with the invention, a method is provided for coating at least a portion of the exposed surface of a metal which comprises:

a) applying to said surface a curable coating composition comprising an aqueous solution of at least one partially or substantially completely hydrolyzed hydroxyl-functional carbamoyl organosilicon compound which possesses:

(i) at least one hydroxyl group bonded to a carbon atom and at least one carbamoyl group covalently bonded to a silicon atom through a silicon-carbon bond, and (ii) at least one divalent oxygen-containing group possessing at least two silyloxy bonds; and, b) curing the curable coating composition on the surface of the metal to provide an anti-corrosion and/or adhesion promoting coating thereon.

The term "VOC" as used herein designates a volatile organic compound, specifically, an organic compound possessing a boiling point equal to or less than 216° C. at atmospheric pressure as determined by ASTM D 86-96. VOC emissions from products have been, and continue to be, the subject of governmental regulations such as the State of California Air Resources Board Regulations for Reducing Volatile Organic Emissions from Consumer Products, Final Regulations Order, Subchapter 8.5, Consumer Products.

The term "HAP" designates a hazardous air pollutant, specifically, a substance on the United States Environment Protection Agency's list of HAPs. HAP emissions from products have been, and continue to be, the subject of governmental regulations such as the National Emission Standards for Hazardous Air Pollutants: Miscellaneous Coating Manufacturing, 40 CFR Part 63.

The expression "low VOC generating potential" as applied to the hydroxyl-functional carbamoyl organosilicon compounds of the invention refers to such a compound's capacity to generate upon the substantially complete hydrolysis thereof from 0 to no more than 10 weight percent VOC(s) based upon the total weight of the substantially non-hydrolyzed compound. The expression "low HAP generating potential" as applied to the hydroxyl-functional carbamoyl organosilicon compounds of the invention refers to such a compound's capacity to generate upon the substantially complete hydrolysis thereof from 0 to no more than 1 weight percent HAP(s) based upon the total weight of the substantially non-hydrolyzed compound.

The term "curing" as used herein refers to the progressive chemical change by which the partially and/or substantially completely hydrolyzed hydroxyl-functional carbamoyl organosilicon component(s) of the anti-corrosion and/or adhesion promoting coating composition of this invention pass from the solation stage of the freshly applied coating composition to the gelation stage resulting in an insoluble, hardened coating layer. This chemical change, brought about by the condensation (or as it may also be referred to, polycondensation) of

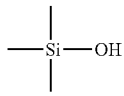

groups with themselves to form the

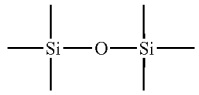

linkages characteristic of organopolysiloxanes, involves the removal of water from the coating composition. The term "curing" includes both partial, or incomplete, curing and substantially complete curing. Condensation resulting in curing will take place under ambient temperature conditions and can be accelerated by the application of heat and/or vacuum.

Other than in the working examples or where otherwise indicated, all numbers expressing amounts of materials, reaction conditions, time durations, quantified properties of materials, and so forth, stated in the specification and claims are to be understood as being modified in all instances by the term "about."

It will also be understood that any numerical range recited herein is intended to include all sub-ranges within that range.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof

DETAILED DESCRIPTION OF THE INVENTION

A. Hydroxyl-Functional Carbamoyl Organosilicon Compounds

In one embodiment of the invention, the hydroxyl-functional carbamoyl organosilicon compound is represented by general Formula (1):

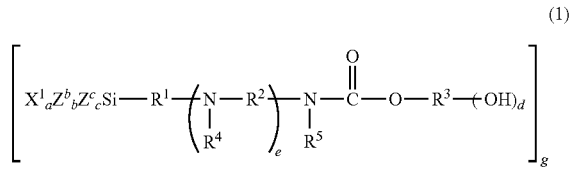

wherein:
each occurrence of $R^1$, $R^2$ and $R^3$ is independently a divalent hydrocarbylene group, e.g., an alkylene, alkenylene, arenylene or aralkylene group of up to 12 carbon atoms, optionally containing one or more etheric oxygen atoms;

each occurrence of $R^4$ is independently hydrogen, a hydrocarbyl group, e.g., an alkyl, alkenyl, arenyl, aryl or aralkyl group of up to 8 carbon atoms, an —$R^1SiX^1_aZ^b_bZ^c_c$ group or a —$C(=O)OR^6(OH)_f$ group;

each occurrence of $R^5$ is independently hydrogen, a hydrocarbyl group, e.g., an alkyl, alkenyl, arenyl, aryl or aralkyl group of up to 8 carbon atoms, or an —$R^1SiX^1_aZ^b_bZ^c_c$ group;

each occurrence of $R^6$ is independently a divalent or polyvalent hydrocarbylene group, e.g., a divalent alkylene, alkenylene, arenylene, arylene or aralkylene group of up to 12 carbon atoms;

each occurrence of $X^1$ is independently —Cl, —Br, $R^7O$—, $R^7C(=O)O$—, $R^7_2C=NO$—, $R^7_2NO$—, $R^7_2N$—, —$R^7$, or $(HO)_{h-1}R^8O$— wherein each $R^7$ is independently hydrogen or a hydrocarbyl group, e.g., an alkyl, alkenyl, aryl or aralkyl group of up to 18 carbon atoms, optionally containing one or more etheric oxygen atoms, and each $R^8$ is independently a divalent or polyvalent hydrocarbylene group, e.g., an alkylene, alkenylene, arenylene, arylene or aralkylene group of up to 15 carbon atoms, optionally containing one or more etheric oxygen atoms;

each occurrence of $Z^b$, which forms a bridging structure between two silicon atoms, is independently [—$OR^9(OH)_{i-2}$O—]$_{0.5}$ or [—O—]$_{0.5}$ wherein each occurrence of $R^9$ is independently a divalent or polyvalent hydrocarbylene group, e.g., an alkylene, alkenylene, arenylene, arylene or aralkylene group of up to 15 carbon atoms, optionally containing one or more etheric oxygen atoms;

each occurrence of $Z^c$, which forms a cyclic structure with a silicon atom, is independently a —$OR^{10}(OH)_{j-2}$O— group wherein $R^{10}$ is independently a divalent or polyvalent hydrocarbylene group, e.g., an alkylene, alkenylene, arenylene, arylene or aralkylene group of up to 15 carbon atoms, optionally containing one or more etheric oxygen atoms; and, subscripts a, b, c, d, e, f, g and h are integers wherein a is 0 to 2; b is 0 to 3; c is 0 or 1; d is 1 to 4; e is 0 to 20, f is 1 to 4; g is 1 to 100; h is 2 to 3; i is 2 to 3 and j is 2 to 3, provided, when c is 1, a+b is 1; and, when b is 0, then g is 1 and c is 1.

As used herein in connection with the hydroxyl-functional carbamoyl organosilicon composition of Formula (1), "alkyl" includes straight, branched and cyclic alkyl groups; "alkenyl" includes any straight, branched, or cyclic alkenyl group containing one or more carbon-carbon double bonds where a site of substitution, if any, can be either at a carbon-carbon double bond or elsewhere in the group; "aryl" includes any aromatic hydrocarbon from which one hydrogen atom has been removed; "aralkyl" includes any of the aforementioned alkyl groups in which one or more hydrogen atoms have been substituted by the same number of like and/or different aryl (as defined herein) substituents; "arenyl" includes any of the aforementioned aryl groups in which one or more hydrogen atoms have been substituted by the same number of like and/or different alkyl (as defined herein) substituents; "alkylene" includes straight, branched and cyclic alkylene groups; "alkenylene" includes any straight, branched, or cyclic alkenylene group containing one or more carbon-carbon double bonds where a site of substitution, if any, can be either at a carbon-carbon double bond or elsewhere in the group; "arylene" includes any aromatic hydrocarbon from which two or more hydrogen atom have been removed; "aralkylene" includes any of the aforementioned alkylene groups in which one or more hydrogen atoms have been substituted by the same number of like and/or different aryl (as defined herein) substituents; "arenylene" includes any of the aforementioned arylene groups in which one or more hydrogen atoms have been substituted by the same number of like and/or different alkyl (as defined herein) substituents; "hydrocarbyl" includes any hydrocarbon in which one hydrogen atom has been removed to form a monovalent group, and "hydrocarbylene" includes any hydrocarbon in which at least two hydrogen atoms have been removed to form a divalent or polyvalent group.

Specific examples of alkyl include methyl, ethyl, propyl and isobutyl. Specific examples of alkenyl include vinyl, propenyl, allyl, methallyl, ethylidenyl norbornane, ethylidene norbornyl, ethylidenyl norbornene and ethylidene norbornenyl. Specific examples of aryl include phenyl and naphthalenyl. Specific examples of aralkyl include benzyl and phenethyl. Specific examples of arenyl include tolyl and xylyl. Specific examples of alkylene include methylene, ethylene, propylene and isobutylene. Specific examples of alkenylene include ethenylene, propenylene, methallylene, ethylidenylene norbornane, ethylidene norbornylene, ethylidenylene norbornene and ethylidene norbornenylene. Specific examples of aryl include phenylene and naphthalenylene. Specific examples of aralkylene include phenethylene and phenylmethylene. Specific examples of arenylene include tolylene and xylylene.

As used herein in connection with the hydroxyl-functional carbamoyl organosilicon compositions of Formula (1), "cyclic alkyl", and "cyclic alkenyl" also include bicyclic, tricyclic and higher cyclic structures as well as the aforementioned cyclic structures further substituted with alkyl and/or alkenyl groups. Representative examples of these structures include norbornyl, norbornenyl, ethylnorbornyl, ethylnorbornenyl, ethylcyclohexyl, ethylcyclohexenyl, cyclohexylcyclohexyl and cyclododecatrienyl.

As used herein for $Z^b$, the notations, $(-O-)_{0.5}$ and $[-OR^9(OH)_{i-1}O-]_{0.5}$ refer to one-half of a siloxane bond and one-half of a bridging dialkoxy group, respectively. These notations are used in conjunction with a silicon atom and they are taken herein to mean one-half of an oxygen atom, namely, the half bound to the particular silicon atom, or to one-half of a dialkoxy group, namely, the half bound to the particular silicon atom, respectively. It is understood that the other half of the oxygen atom or dialkoxy group and its bond to silicon occurs somewhere else in the overall molecular structure being described. Thus, the $(-O-)_{0.5}$ siloxane groups and the $[-OR^9(OH)_{i-2}O-]_{0.5}$ dialkoxy groups mediate the chemical bonds that hold two separate silicon atoms together whether these two silicon atoms occur intermolecularly or intramolecularly. In the case of $[-OR^9(OH)_{i-2}O-]_{0.5}$, if the hydrocarbylene group $R^9$ is unsymmetrical, either end of $[-OR^9(OH)_{i-2}O-]_{0.5}$ may be bound to either of the two silicon atoms required to complete the structure of the hydroxyl-functional carbamoyl organosilicon compound.

As used herein for $Z^c$, the notation $-OR^{10}(OH)_{j-2}O-$ refers to one-half of a dialkoxy group. This notation is used in conjunction with a silicon atom and it is taken herein to mean one-half of a dialkoxy group, namely, the half bound to the particular silicon atom to form a silyloxy bond (Si—O) and the other half of the dialkoxy group and its bond to the same silicon atom thus forming a cyclic structure containing a silicon atom.

In another embodiment of the invention, the hydrolyzable hydroxyl-functional carbamoyl organosilicon compound can comprise one or more oligomers of Formula (1) in which g is greater than 1. Oligomers of the hydroxyl-functional carbamoyl organosilicon compound can also result from inter-molecular transesterification of the hydroxyl on the $(-)_2NC(=O)OR^3(OH)_d$ and/or the $(-)_2NC(=O)OR^6(OH)_f$ group with the silyl group of a different hydroxyl-functional carbamoyl organosilicon compound.

Oligomers of the hydroxyl-functional carbamoyl organosilicon compound of Formula (1) can further result from the hydrolysis of the hydroxyl-functional carbamoyl organosilicon compound and the inter-molecular condensation of the hydrolysis products (silanols) of one hydroxyl-functional carbamoyl organosilicon compound with the silanol of a different hydroxyl-functional carbamoyl organosilicon compound such as any of those described herein.

Hydrolysis occurs when water reacts with the hydrolyzable silyl group, e.g.,

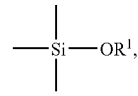

and replaces the hydrolyzable moiety in the group with HO— to provide a silanol,

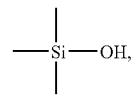

group. Condensation occurs when a silyloxy group,

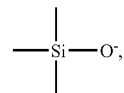

replaces an alkoxy or hydroxy group to provide a siloxane,

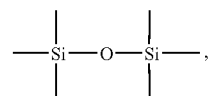

group. The extent of hydrolysis may be calculated using Equation (I):

Percent hydrolysis=$[100\%][1-(A/(A+B+C))]$     (I)

wherein A is the number of hydrolyzable silyl groups; B is the number of silanol groups; and C is the number silyloxy groups bonded to a silicon atom.

The numerical values for A, B and C can be determined by $^{29}$Si Nuclear Magnetic Resonance (NMR) which involves obtaining a spectra of the hydroxyl-containing hydrolyzable silane and interpreting the data. In accordance with this procedure, the hydroxyl-containing hydrolyzable silane or an aqueous solution thereof is placed in a 10 mm NMR tube with a capillary tube containing acetone-$d_6$ added for locking purposes. The chemical shifts are externally referenced to tetramethylsilane for $^{29}$Si NMR. An inverse gated decoupling pulse sequence is used with a pulse width of 45-degrees for $^{29}$Si atom. A delay of 360 seconds is used between scans. The acquisition time of 1.4 seconds for $^{29}$Si NMR operating at a field strength of 7.05 T. 59.6 MHz for $^{29}$Si atom correlates to a sweep width of 11627 Hz and a size of 32K. The spectral data are processed using a line band of 2 Hz. Data for $^{29}$Si NMR spectra are collected for 48 hours. The hydrolysis of the silane is monitored by observing an increase in the chemical shift by approximately 1 ppm as an alkoxy group, e.g., a methoxy group, is replaced by a hydroxyl group to result in a silanol group. Condensation of the hydrolyzed silane is observed as a decrease in the chemical shift of approximately 10 ppm for every alkoxy group replaced with a silyloxy group

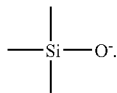

As an alkoxy group is increased in size, e.g., from methoxy to ethoxy, the chemical shift difference increases and can be determined experimentally.

In one embodiment herein, the hydroxyl-functional carbamoyl organosilicon compound(s) and/or aqueous solutions of partially or substantially completely hydrolyzed hydroxyl-functional carbamoyl organosilicon compound(s) can include at least one member selected from the group consisting of monomers of Formula (1), i.e., compounds in which g is 1, oligomers obtained by the transesterification of hydroxyl-functional carbamoyl organosilicon compounds of Formula (1) and oligomers obtained from the partial or substantially complete hydrolysis and, optionally, subsequent partial condensation of a hydroxyl-functional carbamoyl organosilicon compound of Formula (1) or a hydroxyl-functional carbamoyl silane compound of general Formula (2):

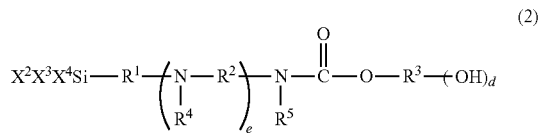

wherein $R^1$, $R^2$, $R^3$, $R^4$, $R^5$, $R^7$, d, and have the aforestated meanings; each occurrence of $X^2$ is independently —Cl, —Br, $R^7O$—, $R^7C(\!=\!O)O$—, $R^7_2C\!=\!NO$—, $R^7_2NO$—, $R^7_2N$—; and each $X^3$ and $X^4$ is independently has one of the aforestated meanings of $X^2$ or $R^7$—.

Partial hydrolysis of the hydroxyl-functional carbamoyl organosilicon compounds of Formula (1) refers to an extent of hydrolysis resulting in replacement of from 1 to 94 mole percent of the $X^1$, [—OR$^9$(OH)$_{i-2}$O—]$_{0.5}$ and —OR$^{10}$(OH)$_{j-2}$O— groups with hydroxyl groups and substantially complete hydrolysis of the hydroxyl-functional carbamoyl organosilicon compounds of Formula (1) refers to an extent of hydrolysis resulting in replacement of from 95 to 100 mole percent of the $X^1$, [—OR$^9$(OH)$_{i-2}$O—]$_{0.5}$ and —OR$^{10}$(OH)$_{j-2}$O— groups with hydroxyl groups. Partial hydrolysis of the hydroxyl-functional carbamoyl organosilicon compounds of Formula (2) refers to an extent of hydrolysis resulting in replacement of from 1 to 94 mole percent of the $X^2$, $X^3$ and $X^4$ groups with hydroxyl groups and substantially complete hydrolysis of the hydroxyl-functional carbamoyl organosilicon compounds of Formula (2) refers to an extent of hydrolysis resulting in replacement of from 95 to 100 mole percent of the $X^2$, $X^3$ and $X^4$ groups with hydroxyl groups.

The partially hydrolyzed hydroxyl-containing hydrolyzable silane has better stability in an aqueous solution because the R$^1$O—Si group terminates the polymerization reaction of the silanol condensation and maintains a lower average molecular weight oligomeric composition that is derived from the hydroxyl-containing hydrolyzable silane. The lower molecular weight oligomeric composition adsorbs more uniformly onto the metal substrate resulting in better adhesion.

The extent of condensation can be determined by the $^{29}$Si Nuclear Magnetic Resonance procedure described above using Equation (II):

Percent condensation=[100%][C/(A+B+C)]    (II)

wherein A is the number of hydrolyzable silyl groups, B is the number of silanol groups and C is the number of silyloxy groups that have replaced an alkoxy or hydroxy group.

The hydroxyl-functional carbamoyl organosilicon compounds of Formula (1) can be prepared by the transesterification of one or more hydrolyzable hydroxyl-functional carbamoyl silanes of Formula (2) with a polyol of Formula (3):

wherein $R^9$ and i have the aforestated meanings, and/or a polyol of Formula (4):

wherein $R^{10}$ and j have the aforestated meanings.

Transesterification can be carried out at sub-ambient, ambient or elevated temperatures, under reduced, ambient or elevated temperature and in the absence or presence of solvents and catalysts. Thus, e.g., transesterification can be carried out at a temperature ranging from 0 to 150° C., preferably from 25° C. to 100° C., and more preferably from 60° C. to 80° C., while maintaining a pressure in the range of from 0.1 to 2000 mm Hg absolute. In another embodiment, the transesterification temperature can range from 30° C. to 90° C. while maintaining a pressure in the range of from 1 to 80 mm Hg absolute. As lower boiling $X^2$H, $X^3$H and $X^4$H by-products form, such as monoalcohols or carboxylic acids, they can be removed from the reaction mixture by distillation. Removal of these by-products helps to drive the transesterification reaction to completion providing product(s) essentially free of VOCs and HAPs. The transesterification reactions can optionally be catalyzed using suitable transesterification catalysts, e.g., optionally strong protic acids whose pK$_a$'s are below 5.0, strong bases whose pK$_b$'s are below 5.0, and transition metal complexes such as complexes of tin, iron, titanium or other metals. These and similar transesterification catalysts suitable for use herein are disclosed, e.g., in "The Siloxane Bond, Physical Properties and Chemical Transformations", M. G. Voronkov, V. P. Mileshkevich and Yu. A. Yuzhelevskii, Consultants Bureau, a division of Plenum Publishing Company, New York (1978), Chapter 5, the entire contents of which are incorporated by reference herein. The acid, base or metal catalyst can be used, e.g., at a level of from 10 ppm to 2 weight percent, preferably from 20 ppm to 1000 ppm, and more preferably from 100 ppm to 500 ppm, based upon the total combined weight of the hydroxyl-functional carbamoyl silane and polyol reactants.

Oligomers derived from the partial or substantially complete hydrolysis and optional subsequent partial condensation of the hydroxyl-functional carbamoyl organosilicon compounds of Formula (1) can be obtained by adding water to the hydroxyl-functional carbamoyl silane(s) of Formula (2). The amount of water reacted with the hydroxyl-functional carbamoyl silane can range from 0.1 to 99.9, preferably from 1 to 50, more preferably from 5 to 25, and most preferably from 10 to 15, weight percent water based on the total combined weight of the hydroxyl-functional carbamoyl silane(s) and water. Oligomers derived from the partial condensation of the hydroxyl-functional carbamoyl silane compound of Formula (2) can be obtained by adding a carboxylic acid to these hydroxyl-functional carbamoyl silanes. The amount of carboxylic acid, such as formic acid, can range from 0.1 to 40 weight percent, and more preferably from 5 to 10 weight percent based upon the total combined weight of the substantially non-hydrolyzed hydroxyl-functional carbamoyl silane(s) and acid reactants. Hydrolysis and partial condensation can be carried out at a temperature ranging from 0 to 150° C., preferably from 25° C. to 100° C. and more preferably from 60° C. to 80° C., while maintaining a pressure in the range of from 0.1 to 2000 mm Hg absolute. In another embodiment, the temperature can range from 30° C. to 90° C. while maintaining a pressure in the range of from 1 to 80 mm Hg absolute. As the lower boiling $X^2H$, $X^3H$ and $X^4H$ hydrolysis by-products are formed, they can be removed from the hydrolysis reaction medium, e.g., by distillation.

Hydrolysis and subsequent partial condensation of the organosilicon compounds of the invention can optionally be catalyzed, e.g., using any of the same catalysts mentioned above and in the amounts indicated for such catalysts.

It is understood that a hydroxyl-functional carbamoyl organosilicon compound of Formula (1) can react with water or carboxylic acid to result in partial or substantially complete hydrolysis of the compound thereby providing a different hydroxyl-functional carbamoyl organosilicon compound in which the $X^1$ group includes at least one hydroxyl (HO—) and/or the $Z^b$ group includes at least one $[—O—]_{0.5}$ group.

In another specific embodiment herein, each $X^1$, $X^2$, $X^3$ and $X^4$ group is independently the same or a different hydrolyzable group such as alkyloxy, acyloxy, alkoxyalkyloxy, alkoxyaryloxy, acyloxyalkyloxy, acyloxyaryloxy or aryloxy. Specific examples of such groups are methoxy, ethoxy, propoxy, isopropoxy, 1-{2-[2-(2-methoxy-ethoxy)-ethoxy]-ethoxy}-propoxy, and the like. Each $X^1$, $X^3$ and $X^4$ is independently the same or different non-hydrolyzable group, such as alkyl or aryl. Specific examples of such groups are methyl, ethyl, phenyl, and the like.

In yet another specific embodiment herein, each $R^1$, $R^2$, $R^3$, $R^8$, $R^9$ and $R^{10}$ group is independently a linear, branched or cyclic alkylene group possessing from 1 to 12, preferably from 2 to 8, and more preferably from 3 to 6, carbon atoms. Representative examples of $R^1$, $R^2$, $R^3$, $R^8$, $R^9$ and $R^{10}$ groups are methylene, ethylene, propylene, isopropylene, butylene, isobutylene, pentylene, isopentylene, hexylene, isohexylene, and the like.

In still another specific embodiment herein, each $R^7$ is hydrogen or an alkyl group of from 1 to 4 carbon atoms; each $R^1$, $R^2$, $R^3$, $R^8$, $R^9$ and $R^{10}$ is a linear alkylene group of from 1 to 12, preferably from 2 to 8, and more preferably from 3 to 6, carbon atoms; each $R^4$ is independently hydrogen, a linear alkyl group of from 1 to 4 carbon atoms or —C(=O)OR$^6$(OH)$_f$ in which each $R^6$ is alkylene of from 2 to 6 carbon atoms; each $R^5$ is independently hydrogen or a linear alkyl group of from 1 to 4 carbon atoms; and, f is 1 or 2.

In other embodiments of the hydroxyl-functional carbamoyl organosilicon compounds herein, $X^1$ is (HO)$_{h-1}R^8O$— or $R^7O$— in which $R^7$ is an alkyl group of from 1 to 3 carbon atoms; $Z^b$ is $[—OR^9(OH)_{i-2}O—]_{0.5}$; $Z^c$ is —OR$^{10}$(OH)$_{j-2}$O—; $R^4$ is hydrogen or —C(=O)OR$^6$(OH)$_f$; $R^5$ is hydrogen; $R^6$, $R^8$, $R^9$ and $R^{10}$ have the aforestated meanings; and, f is 1 or 2; g is 2 to 8; h is 2; i is 2; and, j is 2.

In yet other embodiments of the hydroxyl-functional carbamoyl organosilicon compounds herein, $X^1$ is (HO)$_{h-1}$R$^8$O— or $R^7O$— in which $R^7$ is an alkyl group of from 1 to 3 carbon atoms; $Z^b$ is $[—O—]_{0.5}$; $Z^c$ is —OR$^{10}$(OH)$_{j-2}$O—; $R^4$ is H or —C(=O)OR$^6$(OH)$_f$; $R^5$ is hydrogen; $R^6$, $R^8$, $R^9$ and $R^{10}$ have the aforestated meanings; and b is 1 to 2; f is 1 or 2; g is 2 to 8; h is 2; i is 2; and, j is 2.

In one specific embodiment of the invention, the hydroxyl-functional carbamoyl organosilicon compound will have undergone an intra-molecular transesterification between its silyl group and its hydroxyl group bonded-to-carbon or an inter-molecular transesterification between its silyl group and a hydroxyl group bonded-to-carbon of another molecule of the same or different hydroxyl-functional carbamoyl organosilicon compound. Such transesterifications can lead to the formation of oligomers, such as those described herein, resulting in a build-up in the molecular weight and viscosity of the hydroxyl-functional carbamoyl organosilicon compounds of the invention. However, when later undergoing hydrolysis, these oligomers can break up into smaller molecules exhibiting lower viscosities and higher solubilities in aqueous media containing them.

In one specific embodiment herein, the hydroxyl-functional carbamoyl organosilicon compound is a silane containing at least one hydroxyl group and at least one carbamoyl group, the silane being a derivative of a silane such as an aminoalkoxysilane, amino-bis(alkoxysilane)diaminoalkoxysilane and triaminoalkoxysilane. Some specific examples of such silanes are 4-aminobutyltriethoxysilane, N-(2-aminoethyl)-3-aminopropyltrimethoxysilane, N-(6-aminohexyl) aminopropyltrimethoxysilane, 3-aminopropyldimethylethoxysilane, 3-aminopropylmethyldiethoxysilane, 3-aminopropyltrimethoxysilane, 3-aminopropyltris(methoxyethoxy-ethoxy)silane, aminoisobutylmethyldimethoxysilane, gamma-aminopropyltriethoxysilane, bis-(gamma-trimethoxysilylpropyl)amine, N-2-(vinylbenzylamino)-ethyl-3-aminopropyltrimethoxysilane, N-beta-(amino ethyl)-gamma-aminopropyltriethoxysilane, aminomethyltriethoxysilane, aminomethyldiethoxysilane, gamma-aminoisobutyltrimethoxysilane, 4-aminobutyltrimethoxysilane, N-2-(aminoethyl)-3-aminopropyltris(2-ethylhexoxy)silane, 3-aminopropyldiisopropylethoxysilane, 3-N-methylaminopropyltriethoxysilane, 3-aminopropylphenyldiethoxysilane, 3,3'-aminobis(propyltriethoxysilane) and 3-aminopropylmethyldiethoxysilane.

Processes for making hydroxyl-functional silanes of Formula (2) are known, e.g., as disclosed in U.S. Pat. No. 5,587,502, the entire contents of which are incorporated by reference herein.

Specific examples of hydroxyl-functional carbamoyl organosilicon compounds herein are [3-(2-ethoxy-5-methyl-[1,3,2]dioxasilinan-2-yl)-propyl]-carbamic acid 2-hydroxy-ethyl ester; {3-[2-(3-hydroxy-2-methyl-propoxy)-5-methyl-[1,3,2]dioxasilinan-2-yl]-propyl}-carbamic acid 2-hydroxy-ethyl ester; [3-(2-ethoxy-5-methyl-[1,3]dioxan-2-yl)-propyl]-[3-(2-ethoxy-5-methyl-[1,3,2]dioxasilinan-2-yl)-propyl]-carbamic acid 2-hydroxy-ethyl ester; [3-(2,4,4,6-tetramethyl-[1,3]dioxan-2-yl)-propyl]-[3-(2,4,4,6-tetramethyl-[1,3,2]dioxasilinan-2-yl)-propyl]-carbamic acid 2-hydroxy-ethyl ester; [3-(2,4,4,6-tetramethyl-[1,3]dioxan-2-yl)-propyl]-{[3-(2,4,4,6-tetramethyl-[1,3,2]dioxasilinan-2-yl)-propylamino]-methyl}-carbamic acid 2-hydroxy-ethyl ester; ({(2-hydroxy-ethoxycarbonyl)-[3-(2,4,4,6-tetramethyl-[1,3]dioxan-2-yl)-propyl]-amino}-methyl)-[3-(2,4,4,6-tetramethyl-[1,3,2]dioxasilinan-2-yl)-propyl]-carbamic acid 2-hydroxy-ethyl ester; ({(2,3-dihydroxy-propoxycarbonyl)-[3-(2,4,4,6-tetramethyl-[1,3]dioxan-2-yl)-propyl]-amino}-methyl)-[3-(2,4,4,6-tetramethyl-[1,3,2]dioxasilinan-2-yl)-propyl]-carbamic acid 2,3-dihydroxy-propyl ester; [3-(2,4-dimethyl-[1,3,2]dioxasilinan-2-yl)-propyl]-{[[3-(2,4-dimethyl-[1,3,2]dioxasilinan-2-yl)-propyl]-(2-hydroxy-1-methyl-ethoxycarbonyl)-amino]-methyl}-carbamic acid 3-hydroxy-1-methyl-propyl ester; [3-(2,4-dimethyl-[1,3,2]dioxasilinan-2-yl)-propyl]-{[[3-(2,4-dimethyl-[1,3,2]dioxasilinan-2-yl)-propyl]-(2-hydroxy-1-methyl-ethoxycarbonyl)-amino]-methyl}-carbamic acid 3-hydroxy-1-methyl-propyl ester; [4-(2-ethoxy-4-methyl-[1,3,2]dioxasilinan-2-yl)-butyl]-[3-(2-ethoxy-4-methyl-[1,3,2]dioxasilinan-2-yl)-propyl]-carbamic acid 3-hydroxy-1-hydroxymethyl-propyl ester; {3-[2-(3-{2-[3-(2-hydroxy-ethoxycarbonylamino)-propyl]-[1,3,2]dioxasilinan-2-yloxy}-propoxy)-[1,3,2]dioxasilinan-2-yl]-propyl}-carbamic acid 3-hydroxy-propyl ester; {3-[bis-(3-{2-[3-(2-hydroxy-ethoxycarbonylamino)-propyl]-[1,3,2]dioxasilinan-2-yloxy}-propoxy)-3-hydroxypropoxy-silanyl]-propyl}-carbamic acid 3-hydroxy-propyl ester; {3-[{3-[[3-(2-hydroxy-ethoxycarbonylamino)-propyl]-(3-hydroxy-propoxy)-methyl-silanyloxy]-propoxy}-(3-hydroxy-propoxy)-methyl-silanyl]-propyl}-carbamic acid 2-hydroxy-ethyl ester; {[ethyl-[3-{ethyl-[(2-hydroxy-ethoxycarbonylamino)-methyl]-(3-hydroxy-propoxy)-silanyloxy]-propoxy}-(3-hydroxy-propoxy)-silanyl]-methyl}-carbamic acid 2-hydroxy-ethyl ester; {3-[(2-hydroxy-ethoxycarbonylamino)-methyl]-1,1,3,3-tetrahydroxy-disiloxanylmethyl}-carbamic acid 2-hydroxy-ethyl ester; {3-[(2-hydroxy-ethoxycarbonylamino)-methyl]-1,1,3,3-tetramethyl-disiloxanylmethyl}-carbamic acid 2-hydroxy-ethyl ester; and, {4,6-bis-[(2-hydroxy-ethoxycarbonylamino)-methyl]-2,4,6-trimethyl-[1,3,5,2,4,6]trioxatrisilinan-2-ylmethyl}-carbamic acid 2-hydroxy-ethyl ester.

The hydroxyl-functional carbamoyl organosilicon compounds of the invention can be obtained by partial and/or substantially complete hydrolysis followed by optional partial condensation of a mixture of silanes containing at least one hydroxyl-functional carbamoyl silane as previously described and at least one silane devoid of a hydroxyl group. Examples of such silanes lacking a hydroxyl group are vinyl alkoxysilanes, allylalkoxysilanes, sulfur-containing alkoxysilanes, tetraalkoxy silanes, alkyl alkoxysilanes, haloalkyl alkoxysilanes, aryl alkoxysilanes, alkaryl alkoxysilanes, aralkyl alkoxysilanes, acryloyl and methacryloyl alkoxysilanes, mercaptoalkoxysilanes and aminoalkoxysilanes. Specific silanes of the foregoing and similar kinds are tetraethoxysilane, tetramethoxysilane, tetraisopropoxysilane, methyltrimethoxysilane, ethyltriethoxysilane, hexyltriethoxysilane, cyclohexyltrimethoxysilane, 1,1,1-trifluoroethyltriethoxysilane, phenyltriethoxysilane, phenylmethyldiethoxysilane, phenylmethyldimethoxysilane, diphenyldimethoxysilane, 2-phenylethyltrimethoxysilane, benzyltriethoxysilane, vinyltrimethoxysilane, dimethyldimethoxysilane, trimethylmethoxysilane, diethyldimethoxysilane, allyltrimethoxysilane, divinyldimethoxysilane, methylinyldimethoxysilane, bis(triethoxysilyl)methane, bis(triethoxysilyl)ethane, butenyltrimethoxysilane, 3-bromopropyltrimethoxysilane, 2-chloroethylmethyldimethoxysilane, phenyltrimethoxysilane, 1,2-bis-(trimethoxysilyl)ethane, 1,6-bis-(trialkoxysilyl)hexane, 1,6-bis-(trimethoxysilyl)hexane, 1,2-bis-(triethoxysilyl)ethylene, 1,4-bis-(trimethoxysilylethyl)benzene, and 1,2-bis-(trimethoxysilylpropyl)amine, 4-aminobutyltriethoxysilane, N-(2-aminoethyl)-3-aminopropyltrimethoxysilane, N-(6-aminohexyl)aminopropyltrimethoxysilane, 3-aminopropyldimethylethoxysilane, 3-aminopropylmethyldiethoxysilane, 3-aminopropyltriethoxysilane, 3-aminopropyltrimethoxysilane, 3-aminopropyltris(methoxyethoxy-ethoxy)silane, aminoisobutyltrimethoxysilane, aminoisobutylmethyldimethoxysilane, gamma-aminopropyltriethoxysilane, bis-(gamma-trimethoxysilylpropyl)amine, vinyltriethoxysilane, vinyltripropoxysilane, vinyltriisopropoxysilane, vinyltributoxysilane, vinylacetoxysilane, vinylmethyltrimethoxysilane, vinylethyltrimethoxysilane, vinylpropyltrimethoxysilane, N-2-(vinylbenzylamino)-ethyl-3-aminopropyltrimethoxysilane, N-beta-(amino ethyl)-gamma-aminopropyltriethoxysilane, aminomethyltriethoxysilane, aminomethyldiethoxysilane, gamma-aminoisobutyltrimethoxysilane, methacryloxypropylmethoxysilane, vinyl-tris(2-methoxyethoxy)silane, mercaptopropyl silane, aminoalkoxy silane, 4-aminobutyltriethoxysilane, N-2-(aminoethyl)-3-aminopropyltris(2-ethylhexoxy)silane, 3-aminopropyldiisopropylethoxysilane, 3-N-methylaminopropyltriethoxysilane, 3-aminopropylphenyldiethoxysilane, 3,3'-aminobis(propyltriethoxysilane), N-(3-triethoxysilylpropyl)dibutyl aspartate and 3-aminopropylmethyldiethoxysilane.

B. Anti-Corrosion and/or Adhesion Promoting Coating Compositions

The amount of hydroxyl-functional carbamoyl organosilicon compound present in an anti-corrosion and/or adhesion promoting coating composition of the invention can vary considerably depending on the amount and/or type of monomers of Formula (1), oligomers derived from monomers of Formula (2) or partially or completely hydrolyzed oligomers derived from the monomers of Formula (2), the amount of water or carboxylic acid, as well as the amount and/or type of any additional component of the hydrolysis reaction medium such as surfactant, catalyst, cosolvent, and the like.

The amount of hydroxyl-functional carbamoyl organosilicon compound(s) in the coating compositions herein can also vary over fairly wide limits depending on the desired levels of surface tension, stability and hydrolysis of its organosilicon component(s). Suitable amounts of organosilicon component(s) can vary, e.g., from 0.01 to 50, preferably from 0.1 to 30, and more preferably from 0.5 to 16, weight percent based on the total weight of anti-corrosion and/or adhesion promoting composition. It will be understood herein that concentrations of hydroxyl-functional hydrolyzable silane(s) and hydroxyl-functional carbamoyl organosilicon compound(s) greater than the foregoing can result in a thick (referring to thickness in mass per square area of anti-corrosion and/or adhesion promoting coating(s) herein) anti-corrosion and/or adhesion promoting coatings. Such coating compositions are more costly to manufacture and can be brittle and therefore not very practical. In addition, thick coatings can also reduce the micro-roughness of the metal to which they are applied which decreases the surface area of the metal and may lead to less interaction between the adhesion promoting coating and any further coating thereupon. In one embodiment herein, the applied anti-corrosion and/or adhesion promoting coating composition of the invention can have a dry thickness of from 0.01 to 5, preferably from 0.05 to 2, and more preferably from 0.1 to 1, micrometers.

In one embodiment herein, the hydroxyl-functional carbamoyl organosilicon compound can have a relatively high solubility in aqueous media even up to being fully miscible with the selected aqueous media. Some advantageous solubilities include up to 600 grams per liter (g/l), preferably up to 400 g/l and more preferably up to 300 g/l. In another specific embodiment herein, the hydroxyl-functional carbamoyl organosilicon compounds can be made to possess long-term stability despite thermodynamically favorable condensation processes. In yet a further specific embodiment, oligomers of the hydroxyl-functional carbamoyl organosilicon compounds can exhibit one of the above-described levels of high solubility.

The aqueous solution of the hydroxyl-containing hydrolyzable silane can be partially or substantially fully hydrolyzed and the resulting hydrolysis products can subsequently partially condense to form oligomers through the formation of siloxane bonds (Si—O—Si). These partially condensed products are generally less soluble in water. If the extent of condensation becomes too great, the oligomers or a significant portion of them may become insoluble and as such, unsuitable for use in the metal coating method of the invention.

Useful aqueous coating media generally possesses a level of condensation of the hydroxyl-containing hydrolyzable silane component(s) of from 0 to 95, preferably from 1 to 80, and more preferably from 2 to 50, percent.

The anti-corrosion an/or adhesion promoting coating composition can be prepared using water from any industrially suitable source including tap water, preferably ion-exchanged water, and more preferably distilled water. The amount of water can vary greatly depending on the amount and/or type of hydroxyl-functional carbamoyl organosilicon compound or hydroxyl-functional carbamoyl silane, the amount and/or type of oligomers derived from the foregoing as described above and the amount and/or type of any additional component(s) such as the aforementioned surfactant, catalyst, cosolvent and organic acid. The amount of water in the anti-corrosion and/or adhesion promoting coating composition can also vary depending on the desired levels of surface tension, pH, stability and hydrolysis of the hydroxyl-functional carbamoyl organosilicon compounds therein. Suitable amounts of water include from 50 to 99.9, preferably from 75 to 99, and more preferably from 85 to 98, weight percent based on the total weight of the coating composition.

Examples of surfactants that can be incorporated in the anti-corrosion and/or adhesion promoting coating composition of the invention include polyoxyethylene alkyl ethers, polyoxyethylene alkyl phenyl ethers, polyoxyethylene fatty acid esters, sorbitan fatty acid esters, polyoxyethylene sorbitan fatty acid ester fatty acid salts, alkyl sulfate ester salts, alkyl benzene sulfonates, alkyl phosphates, alkylallyl sulfate ester salts, polyoxyethylene alkylphosphate esters, quaternary ammonium salts, long chain alkyl trimethylammonium salts, long chain alkyl benzyl dimethyl ammonium salts, and di(long chain alkyl) dimethyl ammonium salts, ethoxylated nonyl phenols and polyvinyl alcohols. Specific examples of suitable surfactants include Triton X-100 manufactured by Dow Chemical Company and Silwet* L-77 manufactured by Momentive Performance Materials (provided in the case of the latter, the surfactant is present at a neutral pH). The amount of surfactant employed can vary greatly depending on the amount and/or type of hydroxyl-functional carbamoyl organosilicon compound, the amount and/or type of water and the amount and/or type of any additional component(s) utilized such as catalyst, cosolvent and organic acid. The amount of surfactant can also vary depending on the desired levels of surface tension, pH, stability and hydrolysis of the hydroxyl-functional carbamoyl organosilicon component(s) of the coating composition. Suitable amounts of surfactant where present, are from 0.0001 to 5, preferably from 0.001 to 2, and more preferably from 0.02 to 0.1, weight percent based on the total weight of the anti-corrosion and/or adhesion promoting coating composition.

Stability of the hydroxyl-functional carbamoyl organosilicon compound(s) in the coating composition of the invention can often be increased by the addition thereto of one or more organic cosolvents. Suitable organic cosolvents include alcohols such as the butyl alcohols, glycols, such as ethylene glycol and propylene glycol, ethers, esters, and the like. Organic cosolvent is preferably one which is a non-VOC, non-HAP, e.g., an alcohol such as 3-{2-[2-(2-methoxyethoxy)-ethoxy]-ethoxy}-propan-1-ol or 3-[2-(2-butoxypropoxy)-propoxy]-propan-1-ol, a ketone such as methyl ethyl ketone, a glycol such as hexylene glycol or 2-methyl-1,3-butanediol, an ester such as acetic acid 3-[2-(2-butoxypropoxy)-propoxy]-propyl ester, and the like. The amounts of these and other cosolvents can vary greatly depending on the amount and/or type of hydroxyl-functional carbamoyl organosilicon compound(s), the amount and/or type of water and the amount and/or type of any additional component(s) that may be present in the composition. The amount of cosolvent can also vary based upon the desired levels of surface tension, pH, stability and hydrolysis of the hydroxyl-functional carbamoyl organosilicon component(s) of the coating composition. In general, the amount of organic cosolvent(s) can vary from 0.1 to 50, preferably from 0.5 to 30, and more preferably from 1 to 20, weight percent based on the total weight of the anti-corrosion and/or adhesion promoting coating compositions.

Where a hydroxyl-functional carbamoyl organosilicon has undergone hydrolysis to some extent, a moderate amount of non-VOC, non-HAP hydrolysis by-product(s), e.g. a glycol such as hexylene glycol or 2-methyl-1,3-propanediol, may be produced and, in effect, function as a cosolvent(s) as described above. Such hydrolysis-produced cosolvent(s) can be present in the coating composition within widely varying levels, e.g., at from 0.1 to 50, preferably at from 0.1 to 20, and more preferably at from 0.2 to 6, weight percent based on the total weight of the anti-corrosion and/or adhesion promoting coating composition.

The pH of the coating composition is advantageously maintained so as to minimize the rate of condensation of its partially and/or substantially completely hydrolyzed hydroxyl-functional carbamoyl organosilicon component(s) thereby maximizing the storage stability of the coating composition. The storage stability of a coating composition of the invention refers to the ability of its organosilicon component(s) to remain substantially in solution, or, stated another way, to resist any significant degree of precipitation over a stated period of time and temperature. Controlling the level of pH of the anti-corrosion and/or adhesion promoting coating composition can assist in providing a good level of storage stability, e.g., at least 3 months, preferably at least 4 months, more preferably at least 5 months and most preferably at least 6 months, at ambient temperature. Such levels of stability can generally be achieved by adjusting the pH of the coating composition, e.g., from 2 to 9, preferably from 3 to 8, more preferably from 3 to 7, and most preferably from 3.5 to 6. Desired levels of pH can be achieved by the addition, e.g., of an organic acid, acetic acid, formic acid, citric acid, phosphoric acid, and the like, at suitable levels, e.g., from 0.001 to 2, preferably from 0.001 to 1, and more preferably from 0.01 to 0.2, weight percent based on the total weight of the anti-corrosion and/or adhesion promoting coating composition.

In another specific embodiment of the invention, the aforementioned and similar organic acids can be used to assist in the hydrolysis of the hydroxyl-functional carbamoyl organosilicon component(s) of the coating composition within any one of the above indicated pH ranges. Hydrolysis of hydrolyzable groups on hydroxyl-functional carbamoyl organosilicon compounds occurs much more readily when the pH values are from 3.5 to 6.

A catalyst can be used to promote condensation to accelerate curing of the anti-corrosion and/or adhesion promoting coating composition herein. Examples of suitable condensation catalysts include compounds such as dibutyltin dilaurate, dibutyltin diacetate, dibutylylin maleate, dilauryltin diacetate, dioctyltin diacetate, dibutyltin-bis(4-methylaminobenzoate), dibuyltindilauryl mercaptide and dibutyltin-bis(6-methylaminocaproate). The condensation catalyst may reduce the shelf life of the anti-corrosion and/or adhesion promoting coating. Preferably, latent catalysts are used. Latent catalysts are inactive during storage and are activated by heat, radiation, or evaporation during the curing process. Examples include salts formed from gaseous or high vapor pressure organic bases, e.g., vapor pressures of 20-760 mmHg at atmospheric pressure, such as ammonia or amine, and low vapor pressure carboxylic acids, e.g., vapor pressures below 1 mmHg, such as phthalic acid. The amount of condensation catalyst can vary widely, e.g., from 0.001 to 1, preferably from 0.001 to 0.5, and more preferably from 0.01 to 0.2, weight percent based on the total weight of the anti-corrosion and/or adhesion promoting coating composition.

C. Metal Coating Procedures and Resulting Coated Metals

The method of applying an anti-corrosion and/or adhesion promoting coating composition prepared in accordance with the invention includes applying a coating of the composition as an aqueous medium, optionally containing one or more surfactants, catalysts, cosolvents and organic acid as previously described, to a metal surface, thereafter curing the coating on the metal surface and if desired, applying a paint or other coating composition to the cured anti-corrosion and/or adhesion promoting coating.

The metal to be coated can be provided in the form of a sheet, bar, rod, wire, foil, etc. Specific examples of metals include copper, silver, brass, titanium, titanium alloy, gold, tin, nickel, chromium, tantalum, surface cold-rolled steel, galvanized steel, hot dip galvanized steel, prime steel, aluminum, steel coated with e.g., at least one of zinc, zinc alloy, aluminum, aluminum alloy and iron.

The anti-corrosion and/or adhesion promoting coating composition herein can be applied to the selected metal surface by any suitable known or conventional coating procedure such as roll-coating, specifically reverse roll coating, dip-coating, flood coating and spray and drawdown coating.

The anti-corrosion and/or adhesion promoting coating compositions are cured by removal of the water phase. The curing process can be carried out at a temperature ranging from 15 to 150° C., preferably from 20° C. to 50° C. and more preferably from 25° C. to 30° C., while maintaining a pressure in the range of from 0.1 to 2000 mm Hg absolute. The heat can be provided by an oven, such as a convection oven, or by heat lamps. The temperature can range from 20° C. to 50° C. while maintaining a pressure on the order of from 1 to 80 mm Hg absolute. Passing a stream of air over the surface of the metal substrate containing the anti-corrosion and/or adhesion promoting coating where the air has a velocity of from 0.1 to 25 meters/hour and, advantageously, from 1 to 15 meters/hour, can be utilized to accelerate the evaporation of water and therefore curing.

Curing of the silane component(s) of a freshly applied coating composition involves the reaction of a silanol of one silane molecule with the silanol of another silane molecule accompanied by the generation of water. The percent condensation of the cured coating can range, e.g., from 30 to 100, preferably from 60 to 99, and more preferably from 65 to 95, percent.

In yet another embodiment of the invention, there is provided a metal coated with a cured anti-corrosion and/or adhesion promoting coating composition of the invention and a subsequently applied additional coating, e.g., a paint, exhibiting improved corrosion performance as indicated by reduced creepage measured in accordance with ASTM D 1654. One paint that is particularly useful herein as a secondary coating is a polyester based paint such as Permaclad 2400 available from Sherwin Williams. The extent of creepage can vary greatly based upon such factors as the specific paint used, exposure time, nature of the underlying adhesion promoting coating, and other factors familiar to those skilled in the art. Besides paint, other coating compositions that can be applied to the cured anti-corrosion and/or adhesion promoting coating composition herein include decorative coating, marine coatings, maintenance coating, architectural coatings, and the like. The anti-corrosion and/or adhesion promoting coatings can be used to improve adhesion between organic polymer compositions, herein including rubbers, adhesives, sealants, plastics and the like and metals substrates.

The metal to be coated can optionally possess surface hydroxyl groups which will react with silyl groups in the organosilicon component(s) of the anti-corrosion and/or adhesion promoting coating composition of the invention thereby serving as anchoring sites for the coating. Examples of such metals include those mentioned above.

The adhesion of a further applied coating, e.g., a paint, may be improved if the condensation of the underlying silane-based layer is in the range of from 60 to 99, and preferably from 65 to 95, percent. Such improved adhesion may be due to the ability of the further applied coating to wet-out the less than completely condensed silane-based coating and to penetrate into, or swell, the underlying partially condensed coating. A partially condensed coating tends to be somewhat more polar and/or have a lower crosslink density because of the residual hydroxyl (HO—) and/or alkoxy ($R^1O$—) groups. These hydroxyl and/or alkoxy groups may enhance the wettability and swellability of the cured film.

The further applied coating can be applied to the cured silane base coating by any known convention procedures, e.g., roll coating, dip coating, flood coating, spray and drawdown techniques and the like. The dry film thickness of the further applied coating ranges from 0.1 to 100 micrometers, and preferably from 1 to 500 micrometers.

The curing of the anti-corrosion and/or adhesion promoting coating may release into the environment VOCs that are the byproducts of the reaction of hydroxyl-functional carbamoyl organosilicon compounds and water, or other volatile components such as organic solvents, coalescing agents, wetting agents, surfactants, and the like. The amount of VOCs should generally range from 0 to no more than 10 weight percent based upon the total weight of all the components of the anti-corrosion and/or adhesion promoting coating prior to the evaporation of any of its volatile components. The curing of the anti-corrosion and/or adhesion promoting coating may also release into the environment HAPs that are the byproducts of the reaction of hydroxyl-functional carbamoyl organosilicon compounds and water, or other components such as organic solvents, coalescing agents, wetting agents, surfactants, and the like, that are listed on the United States Environmental Protection Agency's list of HAPs. The amount of HAPs should generally range from 0 to no more than 1 weight percent based upon the total weight of all the components of the anti-corrosion and/or adhesion promoting coating prior to the evaporation of any of its volatile components.

D. Examples

Examples 1-4 illustrate the preparation of hydroxyl-functional carbamoyl organosilicon compounds in accordance with the invention and Examples 5 and 6 illustrate the method of applying anti-corrosion and/or adhesion promoting compositions of the invention to a metal surface. Comparative Example 1 illustrates a metal surface coated with a known type of chromate-containing anti-corrosion coating composition.

The metal employed in Examples 5 and 6 was provided in the form of unpolished, cut cold rolled steel (CRS) panels measuring 15.2 centimeters (cm)×10.16 cm×0.08128 cm supplied by ACT Laboratories. Prior to being coated, the test panels were cleaned with an alkaline cleaner in a conventional manner, rinsed with distilled water and blow-dried with nitrogen gas. The coating compositions were applied directly to the test panels by a very fine drawdown wire rod (size #3 from Gardco). The coated panels were dried vertically with excess coating being removed from each panel's s bottom edge. The coatings on the panels were then cured and the cured coatings painted with white H67WC55 high solids polyester backing enamel (Permaclad 2400, Sherwin Williams) to a dry thickness of 1.2 mils. Each panel was then subjected to the ASTM B 117 accelerated corrosion test which involved exposing a panel to a neutral salt spray for 250 hours. The anti-corrosion performance of each panel was then evaluated according to ASTM D 1654.

The adhesion performance of the coating compositions on the panels of Examples 5 and was compared with that of a chromium-sealed immersion zinc phosphate-treated test panel of Comparative Example 1. Specifically, this comparative evaluation consisted of dividing a scribe (metal panel) into 10 intervals of equal length. Due to uneven creepage along the scribe, the creepage was measured at the ends of those intervals. Creepage was reported as the minimum, maximum and average distance from the scribe in millimeters and is presented for each respective test panel in Table 1.

The structural formulas of the hydroxyl-functional hydrolyzable carbamoyl silanes used to prepare the hydroxyl-functional carbamoyl organosilicon compounds employed in the coatings of Examples 5 and 6 are as follows:

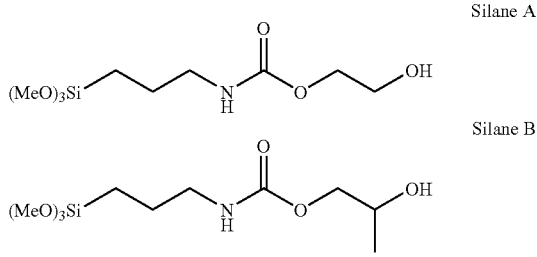

Silane A

Silane B

Comparative Example 1

A commercially purchased chromium-sealed zinc phosphate panel purchased from ACT Test Panel, Inc. was painted with Permaclad 2400. Creepage of the paint on the coated panels was measured and compared with that of the coated panels of Examples 5 and 6. The creepage test results are reported as the minimum, maximum and average distance from the scribe in millimeters in Table 1.

Example 1

3-Aminopropyltrimethoxysilane (20 g, 0.111 mol) was mixed with propylene carbonate (11.39 g, 0.111 mol) under slow stirring. The mixture became slightly warm. Stirring continued for 24 hours to give a hydroxyl-functional hydrolyzable silane. Distilled water (18 g) was added drop-wise under stirring to a mixture of 2-hydroxylpropyl N-(3-trimethoxysilylpropyl)carbamate (15 g), methanol (5 g) and acetic acid (0.1 g) to form a hazy solution. Stirring continued for 12 hours resulting in a clear water-miscible liquid (39.37 wt. % of hydroxyl-functional carbamoyl organosilicon compound(s)).

Example 2

3-Aminopropyltrimethoxysilane (20 g, 0.111 mol) was added to ethylene carbonate (9.82 g, 0.111 mol). The mixture homogenized while stirred and then became slightly warm. Stirring continued for 24 hours to give 2-hydroxylethyl N-(3-trimethoxysilylpropyl)carbamate. Distilled water (18 g) was added drop-wise under stirring to a mixture of 2-hydroxylethyl N-(3-trimethoxysilylpropyl)carbamate (15 g), methanol (5 g) and acetic acid (0.1 g) to form a hazy solution. Stirring continued for 12 hours resulting in clear water-miscible liquid (39.37 wt. % of hydroxyl-functional carbamoyl organosilicon compound(s)).

Example 3

3-Aminopropyltrimethoxysilane (20 g, 0.111 mol) was mixed with propylene carbonate (11.39 g, 0.111 mol) under slow stirring. The mixture became slightly warm. Stirring continued for 24 hours to give 2-hydroxylpropyl N-(3-trimethoxysilylpropyl)carbamate. 2-Methyl-1-3 propanediol (38.8 g, 0.431 mol) was added drop-wise under stirring to a mixture of 2-hydroxylpropyl N-(3-trimethoxysilylpropyl)carbamate (31.4 g, 0.111 mol) and sulfuric acid (0.1 g) and then heated at 50° C. and 15 mm Hg pressure for 4 hours. The methanol that formed was removed by distillation. The product was a clear and slightly viscous liquid.

Example 4

3-Aminopropyltrimethoxysilane (20 g, 0.111 mol) was mixed with ethylene carbonate (9.82 g, 0.111 mol) under slow stirring. The mixture became slightly warm. Stirring continued for 24 hours to give 2-hydroxylethyl N-(3-trimethoxysilylpropyl)carbamate. Hexylene glycol (39.3 g, 0.333 mol) was added drop-wise under stirring to a mixture of 2-hydroxylethyl N-(3-trimethoxysilylpropyl)carbamate (29.8 g, 0.111 mol), and sulfuric acid (0.1 g) and then heated at 50° C. and 15 mm Hg pressure for 4 hours. The methanol that formed was removed by distillation. The product was a clear, low viscosity liquid.

Example 5

An anti-corrosion and/or adhesion promoting coating composition of 2.5 wt. % partial hydrolyzate of $(MeO)_3Si(CH_2)_3NHCOOCH_2CH(Me)OH$ was prepared by mixing 50 mg of a non-ionic surfactant (Triton X-100), 2.54 grams of a 39.37 wt. % aqueous solution of $(MeO)_3Si(CH_2)_3NHCOOCH_2CH(Me)OH$ and 47.41 grams of distilled water. Panels A and B were dried for 20 minutes to cure the coating and thereafter painted with Permaclad 2400.

Due to uneven creepage along the scribe, the scribe was divided into 10 equal intervals and the creepage was measured at the ends of those intervals. The creepage results are reported as the minimum, maximum and average distance from the scribe in millimeters in Table 1.

Example 6

An anti-corrosion and/or adhesion promoting coating of 2.5 wt. % partial hydrolyzate of $(MeO)_3Si(CH_2)_3NHCOOCH_2CH_2OH$ was prepared by mixing 50 mg of a non-ionic surfactant (Triton X-100), 2.54 grams of a 39.37 wt. % aqueous solution of $(MeO)_3Si(CH_2)_3NHCOOCH_2CH_2OH$ and 47.41 grams of distilled water. Panels C and D coated with the coating composition were dried for 20 minutes to cure the coating and thereafter painted with Permaclad 2400.

Due to uneven creepage along the scribe, the scribe was divided into 10 equal intervals and the creepage was measured at the ends of those intervals. The creepage results are reported as the minimum, maximum and average distance from the scribe in millimeters in Table 1.

TABLE 1

| Panel Description | Creepage, mm | | |
|---|---|---|---|
| | Average | Minimum | Maximum |
| $(MeO)_3Si(CH_2)_3NHCOOCH_2CH(Me)OH$ (Panel A), Ex. 5 | 0.9 | 0.5 | 1.5 |
| $(MeO)_3Si(CH_2)_3NHCOOCH_2CH(Me)OH$ (Panel B), Ex. 5 | 1.2 | 0.5 | 2.0 |
| $(MeO)_3Si(CH_2)_3NHCOOCH_2CH_2OH$ (Panel C), Ex 6 | 1.2 | 0.5 | 1.5 |
| $(MeO)_3Si(CH_2)_3NHCOOCH_2CH_2OH$ (Panel D), Ex 6 | 1.2 | 0.5 | 2.5 |
| Chromium-sealed zinc phosphate (Panel of Comp. Ex. 1) | 2.0 | 1.5 | 2.5 |

As these data show, the chromate-free anti-corrosion and/or adhesion promoting coating compositions of the invention (Examples 5 and 6) show equal or better performance in the creepage test than the known Zn—P—Cr coating composition (Comparative Example 1).

It will be understood that while the above description comprises many specifics, these specifics should not be construed as limitations, but merely as exemplifications of specific embodiments thereof. Those skilled in the art will envision many other embodiments within the scope and spirit of the description as defined by the claims appended hereto.

The invention claimed is:

1. A hydroxyl-functional carbamoyl organosilicon compound which possesses:
(i) at least one hydroxyl group bonded to a carbon atom and at least one carbamoyl group covalently bonded to a silicon atom through a silicon-carbon bond, and
    (ii) at least one divalent oxygen-containing group possessing at least two silyloxy bonds, wherein the hydroxyl-functional carbamoyl organosilicon compound is represented by the Formula (1):

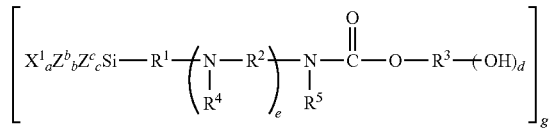

wherein:
each occurrence of $R^1$, $R^2$ and $R^3$ is independently a divalent hydrocarbylene group, optionally containing one or more etheric oxygen atoms;

each occurrence of $R^4$ is independently hydrogen, a hydrocarbyl group, an $—R^1SiX^1_aZ^b_bZ^c_c$ group or a $—C(=O)OR^6(OH)_f$ group where $R^6$ is independently a divalent or polyvalent hydrocarbylene group;

each occurrence of $R^5$ is independently hydrogen, a hydrocarbyl group or an $—R^1SiX^1_aZ^b_bZ^c_c$ group;

each occurrence of $X^1$ is independently —Cl, —Br, $R^7O—$, $R^7C(=O)O—$, $R^7_2C=NO—$, $R^7_2NO—$, $R^7_2N—$, $—R^7$, or $(HO)_{h-1}R^8O—$ wherein each $R^7$ is independently hydrogen or a hydrocarbyl group and each $R^8$ is independently a divalent or polyvalent hydrocarbylene group, optionally containing one or more etheric oxygen atoms;

each occurrence of $Z^b$ is independently $[—OR^9(OH)_{i-2}O—]_{0.5}$ wherein each occurrence of $R^9$ is independently a divalent or polyvalent hydrocarbylene group, optionally containing one or more etheric oxygen atoms, and where $[—OR^9(OH)_{i-2}O—]_{0.5}$ refers to one-half of a bridging dialkoxy group;

each occurrence of $Z^c$ is independently a $—OR^{10}(OH)_{j-2}O—$ group wherein $R^{10}$ is independently a divalent or polyvalent hydrocarbylene group, optionally containing one or more etheric oxygen atoms; and, subscripts a, b, c, d, e, f, g and h are integers wherein a is 0 to 2; b is 0 to 3; c is 0 or 1; d is 1 to 4; e is 0 to 20, f is 1 to 4; g is 1 to 100; h is 2 to 3; i is 2 to 3 and j is 2 to 3, provided, when c is 1, a+b is 1; and when b is 0, then g is 1 and c is 1, wherein said hydroxyl-functional carbamoyl organosilicon compound is selected from the group consisting of [3-(2-ethoxy-5-methyl-[1,3,2]dioxasilinan-2-yl)-propyl]-carbamic acid 2-hydroxy-ethyl ester;

{3-[2-(3-hydroxy-2-methyl-propoxy)-5-methyl-[1,3,2]dioxasilinan-2-yl]-propyl}-carbamic acid 2-hydroxy-ethyl ester;

[3-(2-ethoxy-5-methyl-[1,3]dioxan-2-yl)-propyl]-[3-(2-ethoxy-5-methyl-[1,3,2]dioxasilinan-2-yl)-propyl]-carbamic acid 2-hydroxy-ethyl ester;

[3-(2,4,4,6-tetramethyl-[1,3]dioxan-2-yl)-propyl]-[3-(2,4,4,6-tetramethyl-[1,3,2]dioxasilinan-2-yl)-propyl]-carbamic acid 2-hydroxy-ethyl ester;

[3-(2,4,4,6-tetramethyl-[1,3]dioxan-2-yl)-propyl]-{[3-(2,4,4,6-tetramethyl-[1,3,2]dioxasilinan-2-yl)-propylamino]-methyl}-carbamic acid 2-hydroxy-ethyl ester;

({(2-hydroxy-ethoxycarbonyl)-[3-(2,4,4,6-tetramethyl-[1,3]dioxan-2-yl)-propyl]-amino}-methyl)-[3-(2,4,4,6-tetramethyl-[1,3,2]dioxasilinan-2-yl)-propyl]-carbamic acid 2-hydroxy-ethyl ester;

({(2,3-dihydroxy-propoxycarbonyl)-[3-(2,4,4,6-tetramethyl-[1,3]dioxan-2-yl)-propyl]-amino}-methyl)-[3-(2,4,4,6-tetramethyl-[1,3,2]dioxasilinan-2-yl)-propyl]-carbamic acid 2,3-dihydroxy-propyl ester;

[3-(2,4-dimethyl-[1,3,2]dioxasilinan-2-yl)-propyl]-{[[3-(2,4-dimethyl-[1,3,2]dioxasilinan-2-yl)-propyl]-(2-hydroxy-1-methyl-ethoxycarbonyl)-amino]-methyl}-carbamic acid 3-hydroxy-1-methyl-propyl ester;

[3-(2,4-dimethyl-[1,3,2]dioxasilinan-2-yl)-propyl]-{[[3-(2,4-dimethyl-[1,3,2]dioxasilinan-2-yl)-propyl]-(2-hydroxy-1-methyl-ethoxycarbonyl)-amino]-methyl}-carbamic acid 3-hydroxy-1-methyl-propyl ester;

[4-(2-ethoxy-4-methyl-[1,3,2]dioxasilinan-2-yl)-butyl]-[3-(2-ethoxy-4-methyl-[1,3,2]dioxasilinan-2-yl)-propyl]-carbamic acid 3-hydroxy-1-hydroxymethyl-propyl ester;

{3-[2-(3-{2-[3-(2-hydroxy-ethoxycarbonylamino)-propyl]-[1,3,2]dioxasilinan-2-yloxy}-propoxy)-[1,3,2]dioxasilinan-2-yl]-propyl}-carbamic acid 3-hydroxy-propyl ester;

{3-[bis-(3-{2-[3-(2-hydroxy-ethoxycarbonylamino)-propyl]-[1,3,2]dioxasilinan-2-yloxy}-propoxy)-3-hydroxypropoxy-silanyl]-propyl}-carbamic acid 3-hydroxypropyl ester;

{3-[{3-[[3-(2-hydroxy-ethoxycarbonylamino)-propyl]-(3-hydroxy-propoxy)-methyl-silanyloxy]-propoxy}-(3-hydroxy-propoxy)-methyl-silanyl]-propyl}-carbamic acid 2-hydroxy-ethyl ester;

{[ethyl-{3-[ethyl-[(2-hydroxy-ethoxycarbonylamino)-methyl]-(3-hydroxy-propoxy)-silanyloxy]-propoxy}-(3-hydroxy-propoxy)-silanyl]-methyl}-carbamic acid 2-hydroxy-ethyl ester;

{3-[(2-hydroxy-ethoxycarbonylamino)-methyl]-1,1,3,3-tetrahydroxy-disiloxanylmethyl}-carbamic acid 2-hydroxy-ethyl ester; and {3-[(2-hydroxy-ethoxycarbonylamino)-methyl]-1,1,3,3-tetramethyl-disiloxanylmethyl}-carbamic acid 2-hydroxy-ethyl ester.

2. The hydroxyl-functional carbamoyl organosilicon compound claim 1, wherein said hydroxyl-functional carbamoyl organosilicon compound is

[3-(2-ethoxy-5-methyl-[1,3,2]dioxasilinan-2-yl)-propyl]-carbamic acid 2-hydroxy-ethyl ester;

{3-[2-(3-hydroxy-2-methyl-propoxy)-5-methyl-[1,3,2]dioxasilinan-2-yl]-propyl}-carbamic acid 2-hydroxy-ethyl ester or

[3-(2-ethoxy-5-methyl-[1,3]dioxan-2-yl)-propyl]-[3-(2-ethoxy-5-methyl-[1,3,2]dioxasilinan-2-yl)-propyl]-carbamic acid 2-hydroxy-ethyl ester.

3. The hydroxyl-functional carbamoyl organosilicon compound of claim 1 which upon the substantially complete hydrolysis thereof generates from 0 to no more than 10 weight percent VOC(s).

4. The hydroxyl-functional carbamoyl organosilicon compound of claim 1 which upon the substantially complete hydrolysis thereof generates from 0 to no more than 1 weight percent HAP(s) based upon the total weight of the substantially non-hydrolyzed compound.

5. The hydroxyl-functional carbamoyl organosilicon compound of claim 1 which upon the substantially complete hydrolysis thereof generates from 0 to no more than 10 weight percent VOC(s) and from 0 to no more than 1 weight percent HAP(s) based upon the total weight of the substantially non-hydrolyzed compound.

6. A coating composition comprising an aqueous solution of at least one hydroxyl-functional carbamoyl organosilicon compound of claim 1.

7. A coating composition comprising an aqueous solution of at least one hydroxyl-functional carbamoyl organosilicon compound of claim 2.

8. A coating composition comprising an aqueous solution of at least one hydroxyl-functional organosilicon compound of claim 3.

9. A coating composition comprising an aqueous solution of at least one hydroxyl-functional organosilicon compound of claim 4.

10. A coating composition comprising an aqueous solution of at least one hydroxyl-functional organosilicon compound of claim 5.

11. The coating composition of claim 6 further comprising at least one additional component selected from the group consisting of surfactant, cosolvent, pH modifier and curing catalyst.

12. The coating composition of claim 7 further comprising at least one additional component selected from the group consisting of surfactant, cosolvent, pH modifier and curing catalyst.

13. The coating composition of claim 8 further comprising at least one additional component selected from the group consisting of surfactant, cosolvent, pH modifier and curing catalyst.

14. The coating composition of claim 9 further comprising at least one additional component selected from the group consisting of surfactant, cosolvent, pH modifier and curing catalyst.

15. The coating composition of claim 10 further comprising at least one additional component selected from the group consisting of surfactant, cosolvent, pH modifier and curing catalyst.

16. The coating composition of claim 13 wherein the total amount of additional component(s) represents from 0 to no more than 10 weight percent VOC(s) and from 0 to no more than 1 weight percent HAP(s) of the weight of the composition.

17. The coating composition of claim 13 wherein the total amount of additional component(s) represents from 0 to no more than 10 weight percent VOC(s) and from 0 to no more than 1 weight percent HAP(s) of the weight of the composition.

18. The coating composition of claim 13 wherein the total amount of additional component(s) represents from 0 to no more than 10 weight percent VOC(s) and from 0 to no more than 1 weight percent HAP(s) of the weight of the composition.

19. A method for coating at least a portion of the exposed surface of a metal which comprises:
   a) applying to said surface a curable coating composition comprising an aqueous solution of at least one partially or substantially completely hydrolyzed hydroxyl-functional carbamoyl organosilicon compound which possesses:
      (i) at least one hydroxyl group bonded to a carbon atom and at least one carbamoyl group covalently bonded to a silicon atom through a silicon-carbon bond, and
      (ii) at least one divalent oxygen-containing group possessing at least two silyloxy bonds, wherein the hydroxyl-functional carbamoyl organosilicon compound is represented by the Formula (1):

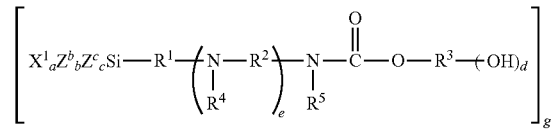

wherein:
   each occurrence of $R^1$, $R^2$ and $R^3$ is independently a divalent hydrocarbylene group, optionally containing one or more etheric oxygen atoms;
   each occurrence of $R^4$ is independently hydrogen, a hydrocarbyl group, an $-R^1SiX^1_aZ^b_bZ^c_c$ group or a $-C(=O)OR^6(OH)_f$ group where $R^6$ is independently a divalent or polyvalent hydrocarbylene group;
   each occurrence of $R^5$ is independently hydrogen, a hydrocarbyl group or an $-R^1SiX^1_aZ^b_bZ^c_c$ group;
   each occurrence of $X^1$ is independently —Cl, —Br, $R^7O-$, $R^7C(=O)O-$, $R^7_2C=NO-$, $R^7_2NO-$, $R^7_2N-$, $-R^7$, or $(HO)_{h-1}R^8O-$ wherein each $R^7$ is independently hydrogen or a hydrocarbyl group and each $R^8$ is independently a divalent or polyvalent hydrocarbylene group, optionally containing one or more etheric oxygen atoms;

each occurrence of $Z^b$ is independently [—$OR^9(OH)_{i-2}$O—]$_{0.5}$ wherein each occurrence of $R^9$ is independently a divalent or polyvalent hydrocarbylene group, optionally containing one or more etheric oxygen atoms, and where [—$OR^9(OH)_{i-2}O$—]$_{0.5}$ refers to one-half of a bridging dialkoxy group;

each occurrence of $Z^c$ is independently a —$OR^{10}(OH)_{j-2}$O— group wherein $R^{10}$ is independently a divalent or polyvalent hydrocarbylene group, optionally containing one or more etheric oxygen atoms; and, subscripts a, b, c, d, e, f, g and h are integers wherein a is 0 to 2; b is 0 to 3; c is 0 or 1; d is 1 to 4; e is 0 to 20, f is 1 to 4; g is 1 to 100; h is 2 to 3; i is 2 to 3 and j is 2 to 3, provided, when c is 1, a+b is 1; and when b is 0, then g is 1 and c is 1; and, b) curing the curable coating composition on the surface of the metal to provide an anti-corrosion and/or adhesion promoting coating thereon.

20. The method of claim 19, wherein:

each occurrence of $R^1$, $R^2$ and $R^3$ is independently an alkylene, alkenylene, arenylene or aralkylene group of up to 12 carbon atoms, optionally containing one or more etheric oxygen atoms;

each occurrence of $R^4$ is independently hydrogen or a —C(=O)$OR^6(OH)$f group;

each occurrence of $R^5$ is hydrogen;

each occurrence of $R^6$ is independently a divalent alkylene, alkenylene, arenylene, arylene or aralkylene group of up to 12 carbon atoms;

each occurrence of $X^1$ is independently $R^7O$— or (HO)$_{h-1}$$R^8O$—, wherein $R^7$ is an alkyl group of from 1 to 3 carbon atoms, and each $R^8$ is an alkylene, alkenylene, arenylene, arylene or aralkylene group of up to 15 carbon atoms, optionally containing one or more etheric oxygen atoms;

each $Z^b$ is [—$OR^9(OH)_{i-2}O$—]$_{0.5}$ wherein $R^9$ is independently an alkylene, alkenylene, arenylene, arylene or aralkylene group of up to 15 carbon atoms, optionally containing one or more etheric oxygen atoms and where [—$OR^9(OH)_{i-2}O$—]$_{0.5}$ refers to one-half of a bridging dialkoxy group;

each $Z^c$ is —$OR^{10}(OH)_{j-2}O$— wherein $R^{10}$ is independently an alkylene, alkenylene, arenylene, arylene or aralkylene group of up to 15 carbon atoms, optionally containing one or more etheric oxygen atoms; and subscripts a, b, c, d, e, f, g and h are integers wherein a is 0 to 2; b is 1 to 3; c is 0 or 1; d is 1 to 4; e is 0 to 20, f is 1 or 2; g is 2 to 8; h is 2; i is 2 and j is 2, provided, when c is 1, a+b is 1.

21. The method of claim 17, wherein:

each occurrence of $R^1$, $R^2$ and $R^3$ is independently an alkylene group of up to 12 carbon atoms;

each occurrence of $R^4$ is independently hydrogen or a —C(=O)$OR^6(OH)_f$ group;

each occurrence of $X^1$ is independently $R^7O$— or (HO)$_{h-1}$$R^8O$—, wherein $R^7$ is an alkyl group of from 1 to 3 carbon atoms, and each $R^8$ is an alkylene group of up to 15 carbon atoms;

each $Z^b$ is [—$OR^9(OH)_{i-2}O$—]$_{0.5}$ wherein $R^9$ is independently an alkylene group of up to 15 carbon atoms, and where —$OR^9(OH)_{i-2}O$— refer to one-half of a bridging dialkoxy group;

each $Z^c$ is —$OR^{10}(OH)_{j-2}O$— wherein $R^{10}$ is independently an alkylene group of up to 15 carbon atoms; and subscripts a, b, c, d, e, f, g and h are integers wherein a is 0 to 1; b is 0; c is 1; d is 1 to 4; e is 0; g is 1; h is 2; i is 2 and j is 2.

22. The method of claim 20 wherein the hydroxyl-functional carbamoyl organosilicon compound includes at least one oligomer thereof.

23. The method of claim 19 wherein the hydroxyl-functional carbamoyl organosilicon compound is at least one compound selected from the group consisting of

[3-(2-ethoxy-5-methyl-[1,3,2]dioxasilinan-2-yl)-propyl]-carbamic acid 2-hydroxy-ethyl ester;

{3-[2-(3-hydroxy-2-methyl-propoxy)-5-methyl-[1,3,2]dioxasilinan-2-yl]-propyl}-carbamic acid 2-hydroxy-ethyl ester;

[3-(2-ethoxy-5-methyl-[1,3]dioxan-2-yl)-propyl]-[3-(2-ethoxy-5-methyl-[1,3,2]dioxasilinan-2-yl)-propyl]-carbamic acid 2-hydroxy-ethyl ester;

[3-(2,4,4,6-tetramethyl-[1,3]dioxan-2-yl)-propyl]-[3-(2,4,4,6-tetramethyl-[1,3,2]dioxasilinan-2-yl)-propyl]-carbamic acid 2-hydroxy-ethyl ester;

[3-(2,4,4,6-tetramethyl-[1,3]dioxan-2-yl)-propyl]-{[3-(2,4,4,6-tetramethyl-[1,3,2]dioxasilinan-2-yl)-propylamino]-methyl}-carbamic acid 2-hydroxy-ethyl ester;

({(2-hydroxy-ethoxycarbonyl)-[3-(2,4,4,6-tetramethyl-[1,3]dioxan-2-yl)-propyl]-amino}-methyl)-[3-(2,4,4,6-tetramethyl-[1,3,2]dioxasilinan-2-yl)-propyl]-carbamic acid 2-hydroxy-ethyl ester;

({(2,3-dihydroxy-propoxycarbonyl)-[3-(2,4,4,6-tetramethyl-[1,3]dioxan-2-yl)-propyl]-amino}-methyl)-[3-(2,4,4,6-tetramethyl-[1,3,2]dioxasilinan-2-yl)-propyl]carbamic acid 2,3-dihydroxy-propyl ester;

[3-(2,4-dimethyl-[1,3,2]dioxasilinan-2-yl)-propyl]-{[[3-(2,4-dimethyl-[1,3,2]dioxasilinan-2-yl)-propyl]-(2-hydroxy-1-methyl-ethoxycarbonyl)-amino]-methyl}-carbamic acid 3-hydroxy-1-methyl-propyl ester;

[3-(2,4-dimethyl-[1,3,2]dioxasilinan-2-yl)-propyl]-{[[3-(2,4-dimethyl-[1,3,2]dioxasilinan-2-yl)-propyl]-(2-hydroxy-1-methyl-ethoxycarbonyl)-amino]-methyl}-carbamic acid 3-hydroxy-1-methyl-propyl ester;

[4-(2-ethoxy-4-methyl-[1,3,2]dioxasilinan-2-yl)-butyl]-[3-(2-ethoxy-4-methyl-[1,3,2]dioxasilinan-2-yl)-propyl]-carbamic acid 3-hydroxy-1-hydroxymethyl-propyl ester;

{3-[2-(3-{2-[3-(2-hydroxy-ethoxycarbonylamino)-propyl]-[1,3,2]dioxasilinan-2-yloxy}-propoxy)-[1,3,2]dioxasilinan-2-yl]-propyl}-carbamic acid 3-hydroxy-propyl ester;

{3-[bis-(3-{2-[3-(2-hydroxy-ethoxycarbonylamino)-propyl]-[1,3,2]dioxasilinan-2-yloxy}-propoxy)-3-hydroxypropoxy-silanyl]-propyl}-carbamic acid 3-hydroxy-propyl ester;

{3-[{3-[[3-(2-hydroxy-ethoxycarbonylamino)-propyl]-(3-hydroxy-propoxy)-methyl-silanyloxy]-propoxy}-(3-hydroxy-propoxy)-methyl-silanyl]-propyl}-carbamic acid 2-hydroxy-ethyl ester;

{[ethyl-{3-[ethyl-[(2-hydroxy-ethoxycarbonylamino)-methyl]-(3-hydroxy-propoxy)-silanyloxy]-propoxy}-(3-hydroxy-propoxy)-silanyl]-methyl}-carbamic acid 2-hydroxy-ethyl ester;

{3-[(2-hydroxy-ethoxycarbonylamino)-methyl]-1,1,3,3-tetrahydroxy-disiloxanylmethyl}-carbamic acid 2-hydroxy-ethyl ester; and {3-[(2-hydroxy-ethoxycarbonylamino)-methyl]-1,1,3,3-tetramethyl-disiloxanylmethyl}-carbamic acid 2-hydroxy-ethyl ester.

24. The method of claim 19 wherein the hydroxyl-functional carbamoyl organosilicon compound upon the substantially complete hydrolysis thereof generates from 0 to no more than 10 weight percent VOC(s) and from 0 to no more than 1 weight percent HAP(s) based upon the total weight of the substantially non-hydrolyzed compound.

25. The method of claim 20 wherein the hydroxyl-functional carbamoyl organosilicon compound upon the substantially complete hydrolysis thereof generates from 0 to no more than 10 weight percent VOC(s) and from 0 to no more than 1 weight percent HAP(s) based upon the total weight of the substantially non-hydrolyzed compound.

26. The method of claim 22 wherein the hydroxyl-functional carbamoyl organosilicon compound upon the substantially complete hydrolysis thereof generates from 0 to no more than 10 weight percent VOC(s) and from 0 to no more than 1 weight percent HAP(s) based upon the total weight of the substantially non-hydrolyzed compound.

27. The method of claim 19 wherein the coating composition further comprises at least one additional component selected from the group consisting of surfactant, cosolvent, pH modifier and curing catalyst.

28. The method of claim 20 wherein the coating composition further comprises at least one additional component selected from the group consisting of surfactant, cosolvent, pH modifier and curing catalyst.

29. The method of claim 22 wherein the coating composition further comprises at least one additional component selected from the group consisting of surfactant, cosolvent, pH modifier and curing catalyst.

30. The method of claim 19 wherein the metal is copper, silver, brass, titanium, titanium alloy, gold, tin, nickel, chromium, tantalum, surface cold-rolled steel, galvanized steel, hot dip galvanized steel, prime steel, aluminum, steel coated with e.g., at least one of zinc, zinc alloy, aluminum, aluminum alloy and iron.

31. The method of claim 19 wherein the cured anti-corrosion and/or adhesion promoting coating possesses a further coating thereon.

32. The method of claim 31 wherein the further coatings is a paint.

33. The coated metal article resulting from the method of claim 19.

34. The coated metal article resulting from the method of claim 31.

* * * * *